US006616946B1

(12) United States Patent
Meier et al.

(10) Patent No.: US 6,616,946 B1
(45) Date of Patent: Sep. 9, 2003

(54) TRIBLOCK COPOLYMER HOLLOW PARTICLES FOR AGENT DELIVERY BY PERMEABILITY CHANGE

(75) Inventors: Wolfgang Meier, Basel (CH); Marc Sauer, Basel (CH)

(73) Assignee: BioCure, Inc., Norcross, GA (US)

( * ) Notice: Subject to any disclaimer, the term of this patent is extended or adjusted under 35 U.S.C. 154(b) by 0 days.

(21) Appl. No.: 09/713,986

(22) Filed: Nov. 15, 2000

Related U.S. Application Data

(60) Provisional application No. 60/165,494, filed on Nov. 15, 1999.

(51) Int. Cl.$^7$ .......................... A61K 9/50; C12N 11/04; C12Q 1/00; G01M 33/545; C07K 17/08
(52) U.S. Cl. ..................... 424/489; 424/490; 424/497; 435/4; 435/178; 435/152; 436/529; 436/531; 530/813; 530/817
(58) Field of Search .................. 435/177, 180, 435/182, 4, 178; 424/489, 490, 497; 436/529, 531; 530/813, 817

(56) References Cited

U.S. PATENT DOCUMENTS

| | | | |
|---|---|---|---|
| 4,548,955 A | 10/1985 | Okahata | |
| 4,925,673 A | 5/1990 | Steiner et al. | 424/455 |
| 5,352,461 A | 10/1994 | Feldstein et al. | 424/493 |
| 5,807,944 A | 9/1998 | Hirt et al. | 526/279 |
| 5,874,316 A | 2/1999 | Cornell et al. | 436/518 |
| 6,071,497 A | 6/2000 | Steiner et al. | 424/45 |
| 6,201,065 B1 | 3/2001 | Pathak et al. | 525/90 |

FOREIGN PATENT DOCUMENTS

| | | |
|---|---|---|
| EP | 274 961 | 7/1988 |
| WO | WO 94/15590 | 7/1994 |
| WO | WO 94/17789 | 8/1994 |
| WO | WO 97/09068 | 3/1997 |
| WO | WO 97/49387 | 12/1997 |

OTHER PUBLICATIONS

US 6,383,501, 5/2002, Wooley et al. (withdrawn)*
Miyauchi E., et al., Microencapsulation, 9(3):329–333 (1992).
Meyer, O. et al., FEBS Letters, 421:61–64 (1998).
Chen, G.H. et al., *Macromol. Chem. Phys.*, 196, 1251–1259 (1995).
Ding, et al., *J. Phys. Chem. B.*, 102, 6107 (1998).
Discher, B. M. et al., *Science* 284, 1143 (1999).
Dobashi, et al., *Langmuir*, 11, 4278 (1995).
Donath, et al., *Angew. Chem. Int. Ed. Engl.*, 110(16):2324 (1998).
Donath, et al., *Nachr. Chem. Tech. Lab.* 47, 400 (1999).
Emmerich et al., *Adv. Mater.* 11(15), 1299 (1999).
Hajduk, D.A. et al., *J. Phys. Chem. B* 102, 4269 (1998).
Hetzer et al, *Angew. Chem. Int. Ed.* 38(13/14), 1962 (1999).
Hoffman, A.S., *Macromol. Symp.*, 98, 645–664 (1995).
Hotz, et al., *Adv. Mater.*, 10, 1387 (1998).
Hotz et al., *Langmuir* 14(5):1031 (1998).
Huang, et al., *J. Am. Chem. Soc.*, 121, 3805 (1999).
Irie, M. et al., *Makromol. Chem., Rapid Commun.*, 5, 829–832 (1985).
Irie, M., *ACS Polym. Preprints*, 27(2), 342–343 (1986).
Kurja, et al., *Polymer*, 34(10), 2045 (1993).
Meier, W., *Macromolecules*, 31, 2212 (1998).
Meier, W., *Langmuir*, 12, 6341 (1996).
Murtagh,et al., *Faraday Discuss. Chem. Soc.*, 81, 127 (1986).
Okubo, et al., *Colloid Polym. Sci.*, 274, 433 (1996).
Poulain, et al., *Polym. Sci.*, 34, 729 (1996).
Sauer et al., *Chem. Commun.* 55 (2000).
Schellenberg et al., *Langmuir* 15, 1283 (1999).
Schmidt, et al., *Polym. Prepr.*,39 725 (1998).
Stewart et al. *Chem. Mater* 11(4), 1048 (1999).
Sukhorukov et al., *Adv. Mater.* 12(2), 112 (2000).
Wang, C, et al., *Nature* 397, 417 (1999).
Wendland et al., *J. Am. Chem. Soc.* 121, 1389 (1999).
Zhang et al., *Science* 272(5269), 1777–9 (1996).

* cited by examiner

*Primary Examiner*—David M. Naff
(74) *Attorney, Agent, or Firm*—Collen A. Beard

(57) ABSTRACT

Polymeric hollow particles for delivery of an agent are provided that change permeability in response to a change in an external stimulus such as pH, temperature, light, ionic strength, electric field, magnetic field and/or solvent composition. The particles can have a shell formed of an amphiphilic triblock ABA or BAB copolymer, where A is a hydrophilic block and B is a hydrophobic block. Low permeability particles with a reversibly permeable shell expand and increase permeability in response to a stimulus so that an active agent such as a therapeutic, prophylactic or diagnostic agent can be introduced. Removing the stimulus allows the particles to return to a low permeability state to form particles loaded with the active agent. Surfaces of the particles can be modified with specific ligands that allow the particles to be directed to a specific target via molecular recognition.

18 Claims, 3 Drawing Sheets

US 6,616,946 B1

TRIBLOCK COPOLYMER HOLLOW PARTICLES FOR AGENT DELIVERY BY PERMEABILITY CHANGE

RELATED APPLICATION

This application claims priority to U.S. Ser. No. 60/165,494, filed on Nov. 15, 1999.

BACKGROUND OF THE INVENTION

The invention is generally in the field of stimulus responsive hollow particles, and more specifically in the area of delivery of active agents using stimulus responsive hollow particles.

Techniques for drug delivery have evolved over the last few decades from simple techniques such as encapsulation of drug within a gelatin capsule, compression of drug into a table for oral delivery, or injection of a solution or suspension of drug, to the use of carriers which modify the time and/or rate of delivery. In perhaps the earliest embodiments, dosage forms were modified through the use of enteric coatings so that oral delivery could be achieved with greater efficiency, especially for drugs that are labile at low pH. Efficiency of release was improved through the use of polymers such as polylactide-co-glycolide that not only protect the drug from certain conditions, but also extend the period of release from less than an hour to hours to days to weeks, depending on the mode of administration. Further improvements in release patterns and efficiency of encapsulation, particularly of insoluble and/or labile drugs, were achieved through the use of improved methods of encapsulation and the use of polymers that degrade by surface erosion rather than bulk erosion. Targeted release has been achieved by coupling of specific ligands to the surface of the encapsulated drug.

Although these techniques have worked well with some drugs, drugs that are extremely labile or insoluble are not encapsulated with good efficiency, or are not released with desired kinetics. Liposomes and other forms of lamellar capsules were developed at about the same time as polymeric dosage forms for enhanced delivery of drugs. Liposomes have the advantages that they are self-assembling and can encapsulate drugs under physiological conditions. Liposomes, however, have undesirable stability characteristics. Techniques such as crosslinking of liposomes and incorporation of targeting molecules have been used to enhance stability and delivery of drug.

Systems where encapsulated drug is released as a function of pH are described in the prior art, using polymers that disaggregate at one pH and aggregate at another. These systems, however, require synthesis of complex polymers (such diketopiperazines and polyamino acids) and form aggregates with the drug to be delivered, rather than fully and easily encapsulating the drug. Moreover, these systems rely upon degradation of the dosage form for release of the drug.

Accordingly, it would be advantageous to have hollow particles for encapsulating and delivering active agents in response to a stimulus.

SUMMARY OF THE INVENTION

The invention is directed to polymeric hollow particles wherein the permeability of the particle changes in response to a change in one or more environmental conditions, such as pH, temperature, light, ionic strength, electric field, magnetic field, solvent composition, etc. The hollow particles are preferably in the nanometer to micrometer size range. The invention is also directed to methods of making and using the responsive hollow particles.

In one embodiment, the shell of the hollow particles is formed from a pH or temperature sensitive polymer. In this embodiment, an important property is the ability to reversibly vary the permeability of the shell forming polymer membrane in response to an external stimulus. This property provides a means to encapsulate and release substances under extremely mild conditions. Loading and release of the substances can be triggered by the external stimulus. For example, the particles can be formed under conditions that result in compressed, or compacted (low permeability) particles. The particles can then be exposed to the stimulus, which causes the particles to expand or otherwise increase their permeability. The active agent can then be introduced into the particles. The stimulus is then removed, or otherwise counteracted, and the particles return to a low permeability state, forming particles that are "loaded" with the active agent.

The particles allow for the encapsulation of low and high molecular weight substances, and even of nanoparticles. Examples include therapeutic, prophylactic, and diagnostic agents, as well as other materials such as cosmetics, dyes or pigments, fragrances, and other compounds with industrial significance. The surface optionally can be modified with specific ligands that allow the particles to be directed to a specific target via molecular recognition.

The invention is also directed to methods for delivery of active agents in response to a stimulus supplied at the point of desired delivery. The methods involve the use of a responsive hollow particle encapsulating the active agent. The hollow particle is designed to be responsive to a stimulus that is present at the intended delivery site or that can be supplied to the intended delivery site. For example, a method for delivery of a drug to the small intestine could involve use of a dosage form including hollow particles that are responsive to the higher pH of the small intestine, relative to the stomach. This may be desirable, for example, for delivery of a drug that is rapidly degraded in the low pH of the stomach.

DETAILED DESCRIPTION OF THE INVENTION

Definitions

Figure 1:
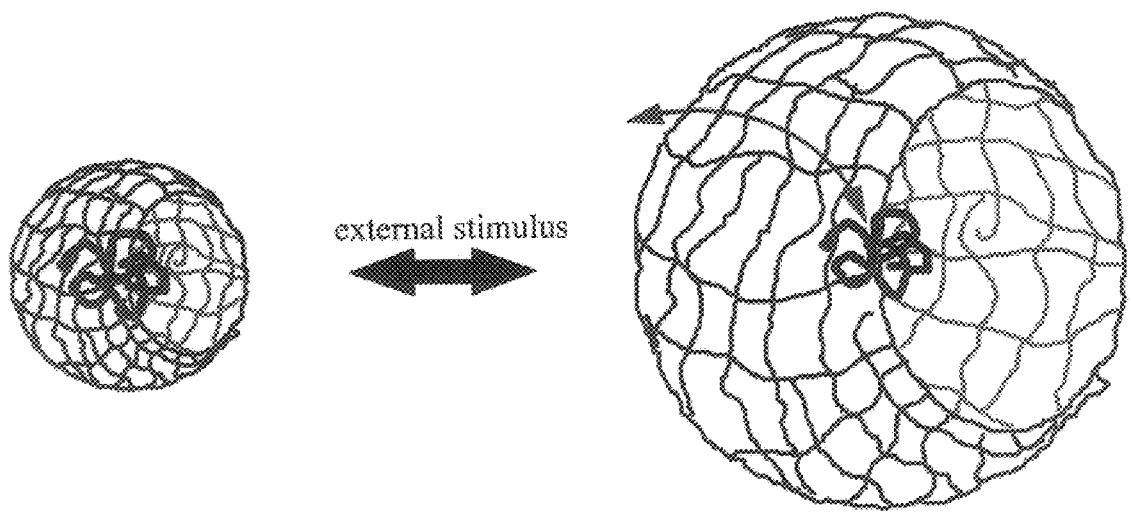
FIG. 1 a schematic of pyrene labeled polyethyleneoxide encapsulated in poly(acrylic acid) hollow particles, showing that the polymeric particle is compressed and of lower permeability at pH 4 and expanded and of higher permeability at pH 9.

"Stimulus" refers to an environmental characteristic such as, but not limited to, pH, temperature, light, ionic strength, electric field, magnetic field, solvent composition, etc. The term "stimulus" as used herein may refer to more than one stimulus.

"Responsive polymer" refers to a polymer having a physical change in response to a stimulus. These polymers have also been referred to as stimuli-responsive, environmentally sensitive, intelligent, or smart polymers.

"Responsive particle" refers to a particle having a permeability change in response to a stimulus.

"Hollow particle" refers to a particle having a hollow core or a core filled with a material to be delivered or released. Particles may have a spherical or other shape.

"Active agent" or "agent" or "drug" refers to a molecule or substance that is encapsulated by a hollow particle. Examples include, but are not limited to, therapeutic, prophylactic, and diagnostic agents, as well as other materials such as cosmetic agents, fragrances, dyes, pigments, photoactive compounds, and chemical reagents, and other compounds with industrial significance. Active agents can also refer to metal particles, biological polymers, nanoparticles, biological organelles, and cell organelles.

The invention is directed to hollow particles that reversibly respond to a stimulus with a change in permeability and methods of making and using such particles. The invention is also directed to methods for delivering active agents to a desired location where they are released in response to a stimulus present at the desired release location.

I. The Responsive Hollow Particles

The particles respond to a stimulus by undergoing a change in permeability. For example, poly(acrylic acid) hollow particles change in size in response to a change in the pH of the solution. At a pH less than 5, the particles are in a compact, contracted state. The acrylic acid groups become increasingly dissociated with an increase in pH, leading to an increase in repulsive electrostatic interactions between the identically charged acrylate groups along the polymer backbone, which results in an expansion of the hollow particles. The particle radius increases from about 20 nm at a pH less than 4 to about 100 nm at a pH greater than 10. This corresponds to an increase of the enclosed volume by a factor of 125. The extent of this expansion depends, at a given pH and ionic strength, on the crosslinking density of the polymer network structure of the shell and on the presence of hydrophobic comonomers. Expansion of a particle results in an increase in its permeability to active agents below a certain size.

Analogous structural changes can be achieved in response to other stimuli, using particles made of appropriate stimulus responsive polymers. For example, a thermosensitive response may be observed for hollow particles of poly(N-isopropylacrylamide) (PNIPAM). Hydrophobic interactions in the neutral PNIPAM particles determine the swelling/deswelling behavior. This should lead to a considerable contraction of such particles with rising temperature. In this case charged comonomers can be used to influence the transition temperature and range.

The stimulus dependent transition influences the permeability of such particles. Pores in the particle shell are opened (or closed) during this transition. This enables free molecular exchange between the interior of the hollow particle and the bulk medium and thus allows encapsulation or release of active agents. The mean size of the pores (and simultaneously the extent of the swelling of the particles) can be directly controlled by the crosslinking density, i.e. the mesh-size of the network structure. Only molecules that are smaller than this mesh-size are able to cross the polymer shell (even in the swollen state).

For the polyelectrolyte hollow particles, the pH and the pH interval necessary for the transition (i.e. the sharpness of the transition) can be systematically influenced using hydrophobic comonomers. Introducing n-butyl-methacrylate comonomers can shift the transition of poly(acrylic acid) hollow particles to higher pH values and, simultaneously, lead to a sharper (a first order-like) transition, occurring in a pH interval of only several tenths of pH units. Similar effects can be achieved in PNIPAM hollow particles using charged comonomers.

Additionally, the surface of polymeric hollow particles can easily be modified with specific ligands. This can be achieved, for example, by copolymerization with a small fraction of ligand-bearing comonomers, e.g. galactosyl-monomers. It is well known that such polymer-bound galactosyl-groups are recognized by the receptors at the surface of hepatocytes (Weigel, et al. *J. Biol. Chem.* 1979, 254, 10830). Such labeled particles can be administered to a patient where they will migrate to and bind to the target.

The responsive hollow particles are made from, or include as a component, a responsive material. The responsive material is desirably a responsive polymer. The hollow particles desirably have a shell made out of the responsive material, solely or in combination with other components. In another embodiment, the hollow particles may include the responsive material in another configuration that controls the permeability of the particle. For example, the responsive material may be in a layer underlying the particle shell or may be interspersed within the particle shell such that it can influence the permeability of the particle in response to the stimulus.

The hollow particles can include other components, such as comonomers added to affect some characteristic of the particles, such as hydrophilicity or hydrophobicity, or targeting molecules on the surface of the particle to direct the particles to a desired target.

The hollow particles to typically range from about 50 nm to about 10 micrometers in diameter, although sizes may range from about 20 nm up to about 100 microns.

A. Responsive Polymers

The particles are formed of a stimulus responsive material, preferably a polymer. The particles can be formed solely of the responsive material. Alternatively, the particles can include the responsive material coupled to or incorporated into the material forming the particle. Alternatively, the responsive material can be located within particles formed of an encapsulating material that is flexible enough to allow the stimulus-responsive material to control its size, permeability, etc. Responsive materials are known and can be readily adapted for use as described herein.

Any of a number of stimulus responsive polymers can be used in the hollow particles. Illustrative temperature, pH, ion, and/or light sensitive polymers are described by Hoffman, A. S., "Intelligent Polymers in Medicine and Biotechnology", *Artif. Organs,* 19, 458–467 (1995); Hoffman, A. S., "Intelligent Polymers in Medicine and Biotechnology", *Macromol. Symp.,* 98, 645–664 (1995); Chen, G. H. et al., "A new temperature- and pH-responsive copolymer for possible use in protein conjugation", *Macromol. Chem. Phys.,* 196, 1251–1259 (1995); Irie, M. et al., "Photoresponsive Polymers. Mechanochemistry of Polyacrylamide Gels having Triphenylmethane Leuco Derivatives", *Makromol. Chem., Rapid Commun.,* 5, 829–832 (1985); and Irie, M., "Light-induced Reversible Conformational Changes of Polymers in Solution and Gel Phase", *ACS Polym. Preprints,* 27(2), 342–343 (1986).

Stimuli responsive oligomers, polymers, and copolymers (referred to herein as "polymers") can be synthesized that range in molecular weight, for example, from about 1,000 to about 30,000 Daltons. The polymers can be derivatized for coupling with other materials, such as targeting ligands.

The selection of monomers and control of molecular weight (by control of reactant concentrations and reaction conditions), structure (e.g. linear homopolymer, linear copolymer, block or graft copolymer, "comb" polymers, and "star" polymers), allow the design of polymers that respond to a specific stimulus and, in some embodiments, to two or more stimuli.

1. Temperature Responsive Polymers

Illustrative of the many different types of temperature responsive polymers are polymers and copolymers of N-isopropyl acrylamide (NIPAAm). PolyNIPAAm is a thermally sensitive polymer that precipitates out of water at 32° C., which is its lower critical solution temperature (LCST), or cloud point. When polyNIPAAm is copolymerized with a more hydrophilic comonomer such as acrylamide, the LCST is higher and the copolymer has a broader temperature range of precipitation. The opposite occurs when it is copolymerized with a more hydrophobic comonomer, such as t-butyl acrylamide, and these copolymers usually are more likely to retain the sharp transition characteristic of PNIPAAm. Accordingly, copolymers can be produced having a desired LCSTs and a desired temperature range of precipitation.

Oligomers of NIPAAm (or other vinyl monomers) having a reactive group at one end can be prepared by the radical polymerization of NIPAAm using AIBN as initiator, plus a chain transfer agent with a thiol (H—SH) group at one end and the desired "reactive" group (e.g. —OH, —COOH, —NH$_2$) at the other end. Chen et al., *Bioconjugate Chem.* 4: 509–514 (1993) and Chen et al., *J. Biomaterials Sci. Polymer Ed.* 5: 371–382 (1994). Appropriate quantities of NIPAAm, AIBN and the chain transfer reagent in DMF are placed in a thick-walled polymerization tube and the mixtures are degassed by freezing and evacuating and then thawing (4 times). After cooling for the last time, the tubes are evacuated and sealed prior to polymerization. The tubes are immersed in a water bath at 60° C. for 4 hours. The resulting polymer is isolated by precipitation into diethyl ether and weighed to determine yield. The molecular weight of the polymer is determined either by titration (if the end group is amine or carboxyl) or by vapor phase osmometry (VPO). If a pH sensitive oligomer or polymer is desired, then acidic monomers such as methacrylic acid or acrylic acid, maleic acid or anhydride, AMPS, or the phosphate ester monomers described above ("Phosmer") can be used, as can basic monomers, such as aminoethyl methacrylate (AEMA), or vinyl formamide, which can be hydrolyzed to polyvinyl amine after polymerization.

The molecular weight of vinyl-type copolymers can be controlled by varying the concentration of the key reactants and the polymerization conditions. However, it is difficult to achieve molecular weights much above about 30 kD using synthesis of vinyl-based oligomers by chain transfer initiation. Further, since the amino-thiol chain transfer agent yields a broader molecular weight distribution than the hydroxyl or carboxyl thiols (which may be undesirable), the —COOH-terminated polymer can be synthesized and the —COOH end group converted to an amine group by activating with carbodiimide and coupling a diamine to the active ester group.

2. pH Responsive Polymers

Synthetic pH sensitive materials are typically based on pH sensitive vinyl monomers, such as acrylic acid (AAc), methacrylic acid (MAAc), maleic anhydride (MAnh), maleic acid (MAc), 2-Acrylamido-2-Methyl-1-Propanesulfonic Acid (AMPS), N-vinyl formamide (NVA), N-vinyl acetamide (NVA) (the last two may be hydrolyzed to polyvinylamine after polymerization), aminoethyl methacrylate (AEMA), phosphoryl ethyl acrylate (PEA), or methacrylate (PEMA). pH sensitive polymers may also be synthesized as polypeptides from amino acids (e.g. polylysine or polyglutamic acid) or derived from naturally occurring polymers such as proteins (e.g. lysozyme, albumin, casein, etc.), or polysaccharides (e.g. alginic acid, hyaluronic acid, carrageenan, chitosan, carboxymethyl cellulose, etc.) or nucleic acids, such as DNA. pH responsive polymers usually contain pendant pH sensitive groups such as —OPO(OH)$_2$, —COOH, or —NH$_2$ groups. With pH responsive polymers, small changes in pH can stimulate phase separation, similar to the effect of temperature on solutions of PNIPAAm. By randomly copolymerizing a thermally sensitive NIPAAm with a small amount (e.g. less than 10 mole percent) of a pH sensitive comonomer such as AAc, a copolymer will display both temperature and pH sensitivity. Its LCST will be almost unaffected, sometimes even lowered a few degrees, at pHs where the comonomer is not ionized, but it will be dramatically raised if the pH sensitive groups are ionized. When the pH sensitive monomer is present in a higher content, the LCST response of the temperature sensitive component may be "eliminated" (e.g. no phase separation seen up to and above 100° C.). Graft and block copolymers of pH and temperature sensitive monomers can be synthesized which retain both pH and temperature transitions independently.

3. Light Responsive Polymers

Light responsive polymers usually contain chromophoric groups pendant to or along the main chain of the polymer and, when exposed to an appropriate wavelength of light, can be isomerized from the trans to the cis form, which is dipolar and more hydrophilic and can cause reversible polymer conformational changes. Other light sensitive compounds can also be converted by light stimulation from a relatively non-polar hydrophobic, non-ionized state to a hydrophilic, ionic state. It is also possible to incorporate multiple environmental sensitivities in the same polymer, such as temperature and light sensitivity, by copolymerization.

In the case of pendant light sensitive group polymers, the light sensitive dye, such as an aromatic azo compound or stilbene derivative, may be conjugated to a reactive monomer and then homopolymerized or copolymerized with other conventional monomers, or copolymerized with temperature sensitive or pH sensitive monomers using chain transfer polymerization as described above. The light sensitive group may also be conjugated to one end of a different stimulus (such as temperature) responsive polymer. A number of protocols for such dye-conjugated monomer syntheses are known. Kungwatchakun et al., supra, and Mamada et al., supra.

Although both pendant and main chain light sensitive polymers may be used, light sensitive polymers and copolymers thereof are typically synthesized from vinyl monomers that contain light sensitive pendant groups. Copolymers of these types of monomers are prepared with "normal" water-soluble comonomers such as acrylamide, or with temperature or pH sensitive comonomers such as NIPAAm or AAc.

Light sensitive compounds may be dye molecules that isomerize or become ionized when they absorb certain wavelengths of light, converting them from hydrophobic to hydrophilic conformations, or they may be other dye molecules that give off heat when they absorb certain wavelengths of light. In the former case, the isomerization alone can cause chain expansion or collapse, while in the latter case the polymer will precipitate only if it is also temperature-sensitive.

Light-responsive polymers usually contain chromophoric groups pendant to the main chain of the polymer. Typical chromophoric groups that have been used are the aromatic diazo dyes. Ciardelli, *Biopolymers* 23: 1423–1437 (1984); Kungwatchakun et al., *Makromol. Chem. Rapid Commun.* 9: 243–246 (1988); Lohmann et al., *CRC Crit. Rev. Therap. Drug Carrier Systems* 5: 263 (1989); Mamada et al., *Macromolecules* 23: 1517 (1990). When this type of dye is exposed to 350–410 nm UV light, the trans form of the aromatic diazo dye, which is more hydrophobic, is isomerized to the cis form, which is dipolar and more hydrophilic, and this can cause polymer conformational changes, causing a turbid polymer solution to clear, depending on the degree of dye-conjugation to the backbone and the water solubility of the main unit of the backbone. Exposure to about 750 nm visible light will reverse the phenomenon. Such light-sensitive dyes may also be incorporated along the main chain of the backbone, such that the conformational changes due to light-induced isomerization of the dye will cause polymer chain conformational changes. Conversion of the pendant due to a hydrophilic or hydrophobic state can also cause individual claims to expand or collapse their conformations. When the polymer main chain contains light sensitive groups (e.g. azo benzene dye) the light-stimulated state may actually contract and become more hydrophilic upon light-induced isomerization.

4. Ion Responsive Polymers

Polysaccharides such as carrageenan that change their conformation, for example, from a random to an ordered conformation, as a function of exposure to specific ions such as K+ or Ca++, can also be used as the stimulus responsive component. Other specific ion sensitive polymers include polymers with pendant ion chelating groups, such as histidine or EDTA, for example.

5. Dual or Multi Stimuli Responsive Polymers

If a light sensitive polymer is also thermally-sensitive, the UV- or visible light-stimulated conversion of a chromophore conjugated along the backbone to a more hydrophobic or hydrophilic conformation can also stimulate the dissolution or precipitation of the copolymer, depending on the polymer composition and the temperature. If the dye absorbs the light and converts it to thermal energies rather than stimulating isomerization, then the localized heating can also stimulate a phase change in a temperature-sensitive polymer such as PNIPAAm, when the system temperature is near the phase separation temperature. The ability to incorporate multiple sensitivities, such as temperature and light sensitivity, along one backbone by vinyl monomer copolymerization lends great versatility to the synthesis and properties of the responsive particles.

Random copolymers of ethylene oxide (EO) and propylene oxide (PO) also have LCSTs or CPs (Bailey and Koleski "Polyethylene Oxide" F. E. Bailey and J. V. Koleske Academic Press, NY (1976)) and have two reactive end groups, so they may be conjugated by one end to other polymers or reactants. Temperature-sensitive block copolyethers are also available from BASF. Triblocks of PEO-PPO-PEO are called Pluronics® or poloxamers, and tetrablocks are called Tetronics® or poloxamines. In the case of EO-PO random or block copolymers, a range of compositions, and molecular weights of these polymers having various reactive end groups can be obtained from Shearwater Polymers, Inc. (Huntsville, Ala.). The compositions are selected on the basis of data available on their cloud points. (Bailey and Koleski and BASF catalog) ("Polyethylene Oxide" F. E. Bailey and J. V. Koleske Academic Press, NY (1976)). A wider range of molecular weights of these copolyethers may be prepared than with the vinyl copolymers, since their synthesis does not use a free radical chain transfer initiation process.

The reactive end group(s) of the oligomer can be derivatized with specific groups (e.g. vinyl sulfone or maleimide) which are selectively reactive with site-specific groups to be conjugated (e.g. the thiol functionality of cysteine). To introduce maleimide or vinyl sulfone groups, an amine-terminated oligomer is preferred. The amine end group of the polymers may be conjugated with maleimide to provide thiol-reactivity. A hydroxyl-terminated polymer can be conjugated with vinyl sulfone by reaction with an excess of divinyl sulfone. The vinyl sulfone end group is typically more hydrolytically stable than the maleimide in conjugation reactions with protein thiol groups. Careful control of reactant stoichiometries and reaction conditions can yield bifunctional vinyl-type polymers such as polyNIPAAm or EO/PO random or block copolymers with different functional groups on each end of the polymer.

6. Block Copolymer Particles

In one embodiment, the particles are made of ABA or BAB triblock or AB diblock amphiphilic copolymers, containing one or more hydrophilic A blocks and one or more hydrophobic B blocks, that self-assemble in water to form hollow particles. A or B, or both, may be a stimulus responsive polymer. Alternatively, a stimulus responsive polymer may be mixed with the self-assembling polymers to form hollow particles, or after formation of the hollow particles. The stimulus responsive polymer may be entrapped within the particles at the time of formation, or chemically or ionically coupled to the amphiphilic polymers forming the self-assembling hollow particles.

The amphiphilic copolymers may be crosslinked or uncrosslinked. In one embodiment the triblock copolymers contain polymerizable end groups and/or side groups that are crosslinked by ionic, covalent, or other bonds to form hollow particles. The particles may have a hydrophobic center, formed either by selection of the copolymers, inclusion of hydrophobic materials within the walls of the hollow particles, or formation of the hollow particles in a hydrophobic medium which is trapped within the vesicle, allowing hydrophobic drugs to be placed in the center of the vesicle. In one such embodiment, the hollow particles are "U-shaped" molecules, with a hydrophobic center and both hydrophilic segments of the amphiphilic copolymer towards the outside.

The formation of hollow particles is a result of the amphiphilic nature of the copolymers. The aggregation in non-crosslinked particles occurs via non-covalent interactions and therefore is reversible. In contrast, the hollow particles which are crosslinked are also held together by covalent bonds, thus the resulting hollow particles are more stable, shape-persistent, and preserve their hollow particle morphology even after they are removed from an aqueous solution.

The stability of a particular vesicle depends in a large part on the strength of the hydrophobic and hydrophilic interactions between the copolymers. The strength also depends upon the stability of the junction between the hydrophilic and hydrophobic segments, and the juncture between the hydrophilic or hydrophobic segment and the polymerizing unit, if one is used. The stability further depends upon the strength of the polymerization or crosslinking. The stability of the vesicle can be decreased by the introduction of weak links, such as biodegradable links or ionic crosslinks, between the hydrophilic and hydrophobic segments, within the hydrophilic or hydrophobic segment, or between the hydrophilic or hydrophobic segment and the polymerizing unit.

The hollow microparticles are formed of amphiphilic segmented copolymers including hydrophilic and hydrophobic segments. The hollow microparticles may also include additional hydrophobic and/or hydrophilic components, as well as crosslinkers such as monomers or macromers with reactive groups, surfactants, and crosslinking initiators, such as photoinitiators.

Suitable polymeric materials are described in U.S. Pat. No. 5,807,944 to Hirt et al. Since these polymers are primarily for use as contact lens, it is highly desirable that the materials be oxygen and ion-permeable. That is not a requirement for other applications, such as drug delivery, and in fact may not be desirable in some applications. Many suitable amphiphilic copolymers and hydrophobic and hydrophilic copolymers are also described in WO 97/49387.

a. Hydrophilic and Hydrophobic Segments

The amphiphilic segmented copolymer includes at least one segment B that includes a hydrophobic polymer. Any of a number of hydrophobic polymers can be used, such as, but not limited to, polysiloxane such as polydimethylsiloxane and polydiphenylsiloxane, perfluoropolyether, polystyrene, polyoxypropylene , polyvinylacetate, polyoxybutylene, polyisoprene, polybutadiene, polyvinylchloride, polyalkylacrylate, polyalkylmethacrylate, polyacrylonitrile, polypropylene, PTHF, polymethacrylates, polyacrylates, polysulfones, polyvinylethers, and poly(propylene oxide), and copolymers thereof.

The hydrophobic segment preferably contains a predominant amount of hydrophobic monomers. A hydrophobic monomer is a monomer that typically gives a homopolymer that is insoluble in water and can absorb less than 10% by weight of water.

Suitable hydrophobic monomers are $C_1$–$C_{18}$ alkyl and $C_3$–$C_{18}$ cycloalkyl acrylates and methacrylates, $C_3$–$C_{18}$ alkylacrylamides and methacrylamides, acrylonitrile, methacrylonitrile, vinyl $C_1$–$C_{18}$ alkanoates, $C_2$–$C_{18}$ alkenes, $C_2$–$C_{18}$ haloalkenes, styrene, (lower alkyl)styrene, $C_4$–$C_{12}$ alkyl vinyl ethers, $C_2$–$C_{10}$ perfluoro-alkyl acrylates and methacrylates and correspondingly partially fluorinated acrylates and methacrylates, $C_3$–$C_{12}$ perfluoroalkylethylthiocarbonylaminoethyl acrylates and methacrylates, acryloxy- and methacryloxyalkylsiloxanes, N-vinylcarbazole, $C_1$–$C_{12}$ alkyl esters of maleic acid, fumaric acid, itaconic acid, mesaconic acid, vinyl acetate, vinyl propionate, vinyl butyrate, vinyl valerate, chloroprene, vinyl chloride, vinylidene chloride, vinyltoluene, vinyl ethyl ether, perfluorohexyl ethylthiocarbonylaminoethyl methacrylate, isobornyl methacrylate, trifluoroethyl methacrylate, hexa-fluoroisopropyl methacrylate, hexafluorobutyl methacrylate, tristrimethylsilyloxysilylpropyl methacrylate (TRIS), and 3-methacryloxypropylpentamethyldisiloxane.

The hydrophobic polymer may include a single type of polymer or more than one type of polymer, such as two or more of those discussed above. The mean molecular weight of one segment B is in the range from about 500 to about 50,000, preferably in the range from about 800 to about 15,000, more preferably in the range of about 1,000 to 12,000, particularly preferably in the range from about 5,000 to about 12,000.

In addition to the hydrophobic segment B, the amphiphilic segmented copolymer includes at least one segment A which includes at least one hydrophilic polymer, such as, but not limited to, polyoxazoline, polyethylene glycol, polyethylene oxide, polyvinyl alcohol, polyvinylpyrrolidone, polyacrylamide, poly(meth)acrylic acid, polyethylene oxide-co-polypropyleneoxide block copolymers, poly(vinylether), poly(N,N-dimethylacrylamide), polyacrylic acid, polyacyl alkylene imine, polyhydroxyalkylacrylates such as hydroxyethyl methacrylate (HEMA), hydroxyethyl acrylate, and hydroxypropyl acrylate, polyols, and copolymeric mixtures of two or more of the above mentioned polymers, natural polymers such as polysaccharides and polypeptides, and copolymers thereof, and polyionic molecules such as polyallylammonium, polyethyleneimine, polyvinylbenzyltrimethylammonium, polyaniline, sulfonated polyaniline, polypyrrole, and polypyridinium, polythiophene-acetic acids, polystyrenesulfonic acids, zwitterionic molecules, and salts and copolymers thereof.

The hydrophilic segment preferably contains a predominant amount of hydrophilic monomers. A hydrophilic comonomer is a monomer that typically gives a homopolymer that is soluble in water or can absorb at least 10% by weight of water.

Suitable hydrophilic monomers are hydroxyl-substituted lower alkyl acrylates and methacrylates, acrylamide, methacrylamide, (lower alkyl) acrylamides and methacrylamides, N,N-dialkyl-acrylamides, ethoxylated acrylates and methacrylates, polyethyleneglycol-mono methacrylates and polyethyleneglycolmonomethylether methacrylates, hydroxyl-substituted (lower alkyl) acrylamides and methacrylamides, hydroxyl-substituted lower alkyl vinyl ethers, sodium vinylsulfonate, sodium styrenesulfonate, 2-acrylamido-2-methylpropanesulfonic acid, N-vinylpyrrole, N-vinyl-2-pyrrolidone, 2-vinyloxazoline, 2-vinyl-4,4'-dialkyloxazolin-5-one, 2- and 4-vinylpyridine, vinylically unsaturated carboxylic acids having a total of 3 to 5 carbon atoms, amino(lower alkyl)— (where the term amino also includes quaternary ammonium), mono(lower alkylamino)(lower alkyl) and di(lower alkylamino)(lower alkyl)acrylates and methacrylates, allyl alcohol, 3-trimethylammonium 2-hydroxypropylmethacrylate chloride (Blemer, QA, for example from Nippon Oil), dimethylaminoethyl methacrylate (DMAEMA), dimethylaminoethylmethacrylamide, glycerol methacrylate, and N-(1,1-dimethyl-3-oxobutyl) acrylamide.

The mean molecular weight of one segment A is in the range from about 500 to about 50,000, preferably in the range from about 800 to about 15,000, more preferably in the range of about 1,000 to 12,000, particularly preferably in the range from about 5,000 to about 12,000.

b. Preparation of the Amphiphilic Copolymer

The segments A and B are linked together through a bond that may be hydrolyzable or non-hydrolyzable. A non-hydrolyzable bond is a covalent bond that is not cleaved by an ordinary aqueous or solvent hydrolysis reaction, e.g. under acidic or basic conditions. Specific bonds that are hydrolyzable are well known to those skilled in the art.

A non-hydrolyzable bond between segments A and B in the amphiphilic segmented copolymer can be formed by polymerizing a suitable hydrophilic monomer (from segment A) in the presence of a suitably functionalized hydrophobic monomer (from segment B) such that a block of units of the hydrophilic monomer grows from the site of functionalization of the hydrophilic monomer or, alternatively by polymerizing a suitable hydrophobic monomer in the presence of a suitably functionalized hydrophilic monomer such that a block of units of the hydrophobic monomer grows from the site of functionalization of the hydrophilic monomer.

The functionalized segment is also called a macroinitiator. Suitable macroinitiators include a thermally or photochemically activatable cationic or anionic groups, or a thermally or photochemically activatable radical initiator group. Anionic polymerization, polycondensation, and polyaddition can also be used. Specific examples of preferred photochemically activatable cationic initiator groups are triflate (—O—$SO_2$—$CF_3$), —I (iodide), —O-mesyl, —O-tosyl, and —$Cl^+$ $AgSbF_6$. The most preferred initiator group is the triflate group. The initiator group is linked to the starting segment in a way that provides a covalent non-hydrolyzable bond between the terminal group of the starting segment and the first monomer forming the growing segment that is attached to the starting segment during the graft copolymerization for preparing the amphiphilic segmented copolymer. Grafting means that polymer chains are grown from a monomer either in terminal or in pendant position onto another preformed polymer.

The initiator group may be introduced into a preformed polymer in a suitable way, for example through linkage of cationic or thermal initiator groups to functional groups present on the starting monomer. Only the latter method is suitable for providing pendent initiator groups. Preferred triflate groups can be introduced by reaction of terminal or pendent functional hydroxyl groups with activated triflic acid derivatives such as ($CF_3$ $SO)_2O$.

A degradable bond between the A segment and the B segment can be used so that the vesicle or nanocapsule can be degraded. Degradable bonds within the A or B segment can also be used. Biodegradable regions can be constructed from polymers or monomers using linkages susceptible to biodegradation. Degradability can be imparted by inclusion of a single degradable linkage or a degradable region made of more than one degradable linkage. The terms degradable linkage and degradable region are used interchangeably hereinafter.

The degradable region is preferably degradable under in vivo conditions. For example, a degradable region may be a hydrolyzable region, such as made from a polymer or oligomer of glycolide, lactide, ε-caprolactone, other hydroxy acids, or other biologically degradable polymer that yields materials that are non-toxic or present as normal metabolites in the body. Regions that are biodegradable by enzymatic degradation can also be used. Preferred poly(α-hydroxy acids) are poly(glycolic acid), poly(DL-lactic acid), and poly(L-lactic acid). Other useful materials include poly (amino acids), poly(anhydrides), poly(orthoesters), poly (phosphazines) and poly(phosphoesters). Polylactones such as poly(ε-caprolactone), poly(δ-valerolactone), and poly(γ-butyrolactone), for example, are also useful. The biodegradable region may have a degree of polymerization ranging from one up to values that would yield a product that is not substantially water soluble. Thus, monomeric, dimeric, trimeric, oligomeric, and polymeric regions may be used.

Accordingly, the amphiphilic segmented copolymers may consist in one embodiment of one segment A and one segment B (A-B-type, diblock), or of one segment A and two segments B attached to its termini (B-A-B-type, triblock), or may have a comb-type structure wherein several segments B are pendent from one segment A, which may further carry one or two terminal segments B). In another embodiment, the amphiphilic segmented copolymers may consist of one segment B and two segments A attached to its termini (A-B-A-type, triblock). In another embodiment, the amphiphilic segmented copolymers may have a comb-type structure wherein several segments A are pendent from one segment B, which may further carry one or two terminal segments A. Preferably, the copolymer is an ABA triblock copolymer.

It is also possible to change the monomer during graft copolymerization such that, for example, first hydrophilic segments A are grown on a preformed hydrophobic segment B and then hydrophobic segments B' are attached to the termini of the earlier prepared segments A. Also a different hydrophilic monomer may be used to produce a different hydrophilic segment A' at the termini of the hydrophilic segments A. Again, other embodiments of the amphiphilic segmented copolymers may be produced starting from a functionalized hydrophilic segment A.

The polymer that makes up the starting segment (A or B) usually has a number average molecular weight Mn in the range from about 500 to about 50,000, preferably in the range from about 800 to about 15,000, more preferably in the range of about 1,000 to 12,000, particularly preferably in the range from about 5,000 to about 12,000. The length of the one or more segments A, B, A', or B' which are to be graft copolymerized on the starting segment can be easily controlled by controlling the amount of monomer (hydrophilic or hydrophobic) which is added for the graft copolymerization. In this way the size of the segments and their ratio can easily be controlled.

The amphiphilic segmented copolymers can be prepared in the presence or absence of a solvent. It is advantageous to use a substantially inert solvent, i.e. one that does not participate in the reaction. Suitable solvents are all solvents which dissolve the monomers used, for example, water, alcohols such as lower alkanols like ethanol or methanol, carboxamides such as dimethylformamide, dipolar aprotic solvents such as dimethyl sulfoxide or methyl ethyl ketone, ketones such as acetone or cyclohexanone, hydrocarbons such as toluene, ethers such as THF, dimethoxyethane or dioxane, halogenated hydrocarbons such as trichloroethane, and mixtures of suitable solvents such as mixtures of water and an alcohol, for example, a water/ethanol or water/methanol mixture.

In the preparation of the amphiphilic segmented copolymers of the invention, the reaction temperature can be, for example, from –60° C. to 150° C., preferably from 0° C. to 80° C. The reaction times are in the range from about 15 minutes to 7 days, preferably in the region of about 2 to 48 hours. If necessary, the reaction is carried out under argon or nitrogen as protective gas. A suitable catalyst, for example dibutyltin dilaurate (DBTDL), is added in the urethane-forming terminal functionalizing reaction.

c. Polymerization Groups

The segmented copolymers may already contain polymerizable groups in the hydrophobic and/or hydrophilic segments, e.g. if a hydrophobic segment B comprises a dienepolymer like polybutadiene or polyisoprene, or if the monomer used for making a hydrophilic segment comprises an unsaturated side chain, for example 2-allyl-oxazoline. Whether or not present, it is possible to introduce polymerizable groups by suitable reactions, e.g. at the end of or pendent from the growing segments. For this purpose, the graft polymerization of the growing segment may be terminated after a suitable chain length is reached and the initiator group present at the chain end capped, for example, either by using specific reagents such as hydroxy styrene, allyl alcohol, HEMA, propargyl alcohol, allyl amines and propargyl amine, or by using KOH/EtOH or primary amines leaving —OH or —NH— groups or unsaturated groups at the end of the growing segment. Hydroxyl groups may also be introduced into the copolymers by employing suitable comonomers in the graft copolymerization, e.g. 2-hydroxyalkyloxazolines. The hydroxyl or —NH— groups may then be reacted, e.g. with an isocyanate carrying a polymerizable unsaturated group. Preferred examples of such bifunctional compounds are 2-isocyanatoethyl methacrylate (IEM), which is especially preferred, and vinyl isocyanate, allyl isocyanate, acryloyl isocyanate, styrene isocyanate, vinyl benzyl isocyanate, propargyl isocyanate, and (meth)acrylic anhydride. Other polymerizable groups can be introduced by methods known to those skilled in the art.

Any type of polymerization/ crosslinking can be used. Examples include photopolymerization, redox polymerization, anionic polymerization, condensation reactions, addition reactions, and chain polymerization reactions.

d. Additional Monomers

In one embodiment of the polymeric particles, the proportion by weight of the amphiphilic segmented copolymer is in the range from 100 to 50%, in particular in the range from 100 to 80%, preferably in the range from 100 to 90%, based on the total polymeric product. The particles may be obtained by direct thermal or photochemical polymerization or crosslinking reaction of the amphiphilic segmented copolymer without the addition of comonomers in the presence of a suitable initiator. However, in some cases, it may be preferable to include a comonomer. Types of comonomers that may be desired include hydrophobic or hydrophilic comonomers, or cationic or anionic comonomers. It may also be desirable to include a comonomer that contains a specific functional group, such as a crosslinkable group, or a group that has a particular affinity for a molecule to be incorporated into or onto the membrane, as discussed below. Suitable hydrophobic and hydrophilic comonomers include those discussed above.

The comonomers can be included within the amphiphilic polymer network, or crosslinked as an interpenetrating or semi-interpenetrating network with the amphiphilic polymer. Crosslinking may be achieved with the addition of a comonomer and/or a crosslinking agent, for example, a polyunsaturated comonomer.

e. Crosslinking Agents

A polymer network can, if desired, be reinforced by addition of a crosslinking agent, for example, a polyunsaturated comonomer. A crosslinked polymeric product including the product of the polymerization and crosslinking reaction of an amphiphilic segmented copolymer, can also be formed, if desired, with at least one vinylic comonomer and with at least one crosslinking agent. Crosslinking can be achieved by a number of different means, such as but not limited to, free radical crosslinking, redox crosslinking, and salt crosslinking.

Examples of suitable crosslinking agents include allyl methacrylate, lower alkylene glycol dimethacrylate, poly(lower alkylene) glycol dimethacrylate, lower alkylene dimethacrylate, divinyl ether, divinyl sulfone, di- and trivinylbenzene, trimethylolpropane trimethacrylate, pentaerythritol tetramethacrylate, bisphenol A dimethacrylate, methylenebis(meth)acrylamide, triallyl phthalate and diallylphthalate, α-ω-bis (methacryloxyalkyl)-oligosiloxanes such as bis(methacryloxypropyl) tetramethyldisiloxane, and perfluoroalkyl- or perfluoroalkylether-bismethacrylates.

The amount of crosslinking agent used is expressed in a proportion by weight based on the total polymer and is in the range from 20 to 0.05%, in particular in the range from 10 to 0.1%, preferably in the range from 5 to 0.1%.

The polymeric products are crosslinked in a manner known in the art from the corresponding monomers (the term monomer here also including an amphiphilic segmented copolymer) by a polymerization reaction customary to the person skilled in the art.

In the case of monomers that can be crosslinked with free radical crosslinking, a mixture of monomers is typically warmed with addition of a free-radical former. Examples of such free-radical formers are azoisobutyronitrile (AIBN), potassium peroxodisulfate, dibenzoyl peroxide, hydrogen peroxide, and sodium percarbonate. If, for example, the compounds are warmed, free radicals form with homolysis, and can then initiate polymerization.

A polymerization reaction may be carried out using a photoinitiator that can initiate free-radical polymerization and/or crosslinking. Examples of suitable photoinitiators include benzoin methyl ether, 1-hydroxycyclohexylphenyl ketone, and Darocure and Irgacure products, preferably Darocure 1173® and Irgacure 2959®. Also suitable are reactive photoinitiators, which can be incorporated, for example, into a macromer, or can be used as a specific comonomer. Examples are described in European Patent No. EP 0 632 329. The photopolymerization can then be initiated by actinic radiation, for example light, in particular UV light having a suitable wavelength. The spectral requirements can, if necessary, be controlled appropriately by addition of suitable photosensitizers.

The polymerizable regions may be polymerizable by photoinitiation by free radical generation, most preferably in the visible or long wavelength ultraviolet radiation. Polymerizable regions are acrylates, diacrylates, oligoacrylates, dimethacrylates, oligomethoacrylates, or other biologically acceptable photopolymerizable groups. A preferred tertiary amine is triethanol amine.

Useful photoinitiators are those that can be used to initiate by free radical generation polymerization of the macromers without cytotoxicity and within a short time frame, minutes at most and most preferably seconds. Preferred dyes as initiators of choice for LWUV initiation are ethyl eosin, 2,2-dimethoxy-2-phenyl acetophenone, other acetophenone derivatives, and camphorquinone. In all cases, crosslinking and polymerization are initiated among copolymers by a light-activated free-radical polymerization initiator such as 2,2-dimethoxy-2-phenylacetophenone or a combination of ethyl eosin ($10^{-4}$–$10^{-2}$ milliM) and triethanol amine (0.001 to 0.1 M), for example.

The choice of the photoinitiator is largely dependent on the photopolymerizable regions. For example, when the macromer includes at least one carbon-carbon double bond, light absorption by the dye causes the dye to assume a triplet state, the triplet state subsequently reacting with the amine to form a free radical that initiates polymerization. Preferred dyes for use with these materials include eosin dye and initiators such as 2,2-dimethyl-2-phenylacetophenone, 2-methoxy-2-phenylacetophenone, and camphorquinone. Using such initiators, copolymers may be polymerized in situ by long wavelength ultraviolet light or by laser light of about 514 nm, for example. Lasers may be used to polymerize any nanospheres from a photopolymerizable solution, due to the precise control that can be achieved with the lasers. It is thus possible to make nanospheres as described herein without inclusion of the amphiphilic polymers.

Initiation of polymerization is accomplished by irradiation with light at a wavelength of between about 200–700 nm, most preferably in the long wavelength ultraviolet range or visible range, 320 nm or higher, most preferably about 514 nm or 365 nm. The light-sensitive free-radical polymerization initiator may be a single compound (e.g. 2,2-dimethoxy-2-phenyl acetophenone) or a combination of a dye and a cocatalyst (e.g., ethyl eosis and triethanol amine).

B. Active Agents

The hollow particles are suitable for delivery of nearly every type of active agent including therapeutic, diagnostic, or prophylactic agents as well as many compounds having cosmetic and industrial use, including dyes and pigments, fragrances, cosmetics, and inks. The agent is delivered to the target site where release occurs as function of change in permeability due to the interaction of a stimulus with the stimulus-responsive material.

Both hydrophilic and hydrophobic drugs, and large and small molecular weight compounds, can be delivered. Drugs can be proteins or peptides, polysaccharides, lipids, nucleic acid molecules, or synthetic organic molecules. Examples of hydrophilic molecules include most proteins and polysaccharides. Examples of hydrophobic compounds include some chemotherapeutic agents such as cyclosporine and taxol. Agents that can be delivered include hormones, chemotherapeutics; antibiotics, antivirals, antifungals, vasoactive compounds, immunomodulatory compounds, vaccines, local anesthetics, antiangiogenic agents, antibodies, neurotransmitters, psychoactive drugs, drugs affecting reproductive organs, and antisense oligonucleotides. Diagnostic agents include gas, radiolabels, magnetic particles, radioopaque compounds, and other materials known to those skilled in the art.

Although described here primarily with reference to drugs, it should be understood that the vesicles can be used for delivery of a wide variety of agents, not just therapeutic or diagnostic agents. Examples include cosmetic agents, fragrances, dyes, pigments, photoactive compounds, and chemical reagents, and other materials requiring a controlled delivery system. Other examples include metal particles, biological polymers, nanoparticles, biological organelles, and cell organelles.

Large quantities of therapeutic substances can be incorporated into the central cavity of the vesicles.

C. Targeting Molecules

The hollow particles can be targeted to a particular site using targeting molecules bound to the surface, or extending from within to the surface, of the hollow particles, where the molecules specifically or preferentially bind to a particular cell or tissue specific site. Examples of targeting molecules include carbohydrates, proteins, folic acid, peptides, peptoids, and antibodies. The list of useful ligands to facilitate binding to mucous type tissues include sialic acid, neuraminic acid, n-acetyl-neuraminic acid, n-glycolylneuraminic acid, 4-acetyl-n-acetylneuraminic acid, diacetyl-n-acetylneuraminic acid, glucuronic acid, iduronic acid, galactose, glucose, mannose, and fucose. Antibodies may be directed to specific cell surface molecules or to antigens expressed when a cell type becomes diseased, for example, a cancer marker.

Stimuli-responsive polymers such as poly(NIPAAm) have been conjugated randomly to affinity molecules, such as monoclonal antibodies, for example, as described in U.S. Pat. No. 4,780,409; Monji and Hoffman, *Appl. Biochem. Biotechnol.* 14: 107–120 (1987). Activated groups (e.g, for conjugating to proteins), were formed randomly along the backbone of PNIPAAm and were conjugated randomly to lysine amino groups on a monoclonal antibody and the conjugate was then applied in a temperature induced phase separation immunoassay. Activated PNIPAAm has also been conjugated to protein A, various enzymes, biotin, phospholipids, RGD peptide sequences, and other interactive molecules. Chen and Hoffman, *Biomaterials* 11: 631–634 (1990); Miura et al., *Abstr. 17th Ann. Meet. Soc. Biomaterials* (1991); Wu et al., *Polymer* 33: 4659–4662 (1992); Chen and Hoffman, *Bioconjugate Chem.* 4: 509–514 (1993); Morris et al., *J. Anal. Biochem.* 41: 991–997 (1993); Park and Hoffman, *J. Biomaterials Sci. Polymer Ed.* 4: 493–504 (1993); Chen and Hoffman, *J. Biomaterials Sci. Polymer Ed.* 5: 371–382 (1994)). Others have also randomly conjugated proteins to PNIPAAm (Nguyen and Luong, *Biotech. Bioeng.* 34: 1186–1190 (1989); Takei et al., *Bioconj. Chem.* 4: 42–46 (1993)) and to pH-sensitive polymers (Fujimura et al., supra). Most of these polymer-protein conjugates involve random lysine amino groups of proteins bound to the polymer through random activated groups pendant along the polymer backbone. The synthesis of an amino-terminated polymer proceeds by the radical polymerization of NIPAAm in the presence of AIBN as an initiator and 1-aminoethanethiol-hydrochloride as a chain transfer reagent. To synthesize a chain with —COOH or —OH terminal groups, carboxyl- or hydroxyl-thiol chain transfer agents, respectively, have been used instead of the aminothiol. It should be noted that the synthesis of the end-reactive polymers is based on a chain transfer initiation and termination mechanism. This yields a relatively short polymer chain, having a molecular weight somewhere between 1000 and 25,000 to 30,000. The shortest chains, less than 10,000 in molecular weight, are usually called "oligomers". Oligomers of different molecular weights can be synthesized by simply changing the ratio of monomer to chain transfer reagent, and controlling their concentration levels, along with that of the initiator.

D. Additional Components

Any of the responsive polymers detailed above may be modified by the addition of additional monomers to add a desired characteristic such as hydrophilicity, hydrophobicity, or a positive or negative charge. For example, one or more hydrophobic or hydrophilic comonomers an be added to alter the pH or temperature responsiveness of a polymer, as discussed above. Suitable comonomers are known to those skilled in the art and are described above with respect to amphiphilic copolymers. Comonomer can be added for other reasons, such as for attachment of a targeting molecule. Comonomers may be added to the responsive polymer itself or added to the particle, such as by mixture with the responsive polymer during formation of the particles.

Moreover, the responsive polymers can be crosslinked after formation thereof by the inclusion of a crosslinkable group in the responsive polymer or otherwise in the responsive particles. Suitable crosslinkable groups and methods are described above in the section on amphiphilic copolymers.

Degradable links or regions can be incorporated into the responsive polymer, or elsewhere into the structure of the hollow particles, so that the particles degrade over a period of time, such as after release of the active agent at the desired location. Suitable degradable links and regions are described above in the section on amphiphilic copolymers.

II. Methods of Using the Responsive Polymer Hollow Particles

The responsive hollow particles can be used for delivery of active agents. The particles are especially suitable for delivery of active agents to an environment, such as a region of a human body, containing the suitable stimulus, or where the suitable stimulus can be applied. The particles may also be used for encapsulation and removal of an active agent from an environment containing the stimulus, or where the stimulus can be applied.

The particles allow for the encapsulation of low and high molecular weight substances, and even of nanoparticles. Examples include therapeutic, prophylactic, and diagnostic agents, as well as other materials such as cosmetics, dyes or pigments, fragrances, and other compounds with industrial significance. The surface optionally can be modified with specific ligands that allow the particles to be directed to a specific target via molecular recognition.

The responsive hollow particles can be used in drug delivery dosage forms for delivery of a wide range of therapeutic, prophylactic, and diagnostic agents. The hollow particles can be used as a stand alone dosage form or can be included as a portion of a more conventional dosage form, such as in a capsule, for example. The hollow particles can be used in combination with other dosage forms to achieve the desired effect, such as in an enteric coated capsule or tablet for example. Dosage forms including the hollow particles can be administered by, e.g., oral, rectal, nasal, or vaginal administration, or can be implanted.

The invention is also directed to methods for delivery of active agents in response to a stimulus supplied at the point of desired delivery. The methods involve the use of a responsive hollow particle encapsulating the active agent. The hollow particle is designed to be responsive to a stimulus known to be present at the intended delivery site. For example, a method for delivery of a drug to the small intestine could involve use of a dosage form including hollow particles that are responsive to the higher pH of the small intestine, relative to the stomach. This may be desirable, for example, for delivery of a drug that is rapidly degraded in the low pH of the stomach.

III. Methods of Making the Responsive Polymer Hollow Particles

Responsive polymers can be made as described above and as known to those skilled in the art. The controlled formation of hollow polymer particles can be achieved using a number of techniques. For example, emulsion, suspension, or interfacial polymerization techniques can be used (see, for example, Kong et al., *Polym. Adv. Technol.* 1996, 274, 633; Emmerich et al., *Adv. Mater.* 1999, 11 1299; Schellenberg et al *Langmuir* 1999, 15, 1283). Self-assembly techniques can be used as discussed above for block copolymers (see, for example, Huang et al., *J. Am. Chem. Soc.* 1999, 121, 8518; Ding et al., *J. Phys. B* 1998, 102 6107; Stewart et al. *Chem Mater* 1999, 11, 34; Hotz et al. *Langmuir*, 1998, 14, 1031; Hotz et al. *Adv. Mater,* 1998, 14, 1031; Murtagh et al., *Farady Discuss. Chem. Soc.,* 1986, 81, 127; Kurja et al. *Polymer,* 1993, 34, 2045; Poulain, et al. *Polym. Sci.,* 1996, 34, 729; Hetzer et al, *Angew. Chem.* 1999,111, 2103).

Templating techniques can also be used (see, for example, Hotz, et al., *Adv. Mater.* 10(16):1387 (1998); Hotz et al., *Langmuir* 14(5):1031 (1998); Donath, et al. *Angew. Chem. Int. Ed. Engl., Adv. Mater* 1999, 1134). Hollow particles can also be made via dendrimers (Wendland et al., *J. Am. Chem. Soc.* 1999, 121 1389).

These methods can lead to the formation of responsive hollow particles if suitable monomers and polymers are used, or a subsequent chemical modification of the resulting particles may render them responsive (e.g. a saponification reaction of poly(tert-butylacrylate) leads to poly(acrylic acid).

In one embodiment, templating techniques are used. The basic concept is to capture the size and shape of a given molecule, particle, or superstructure such that it is preserved in the newly formed species even after removal of the template. Liposomes can be used as templates for formation of the hollow particles. The aqueous core, the lipid-water interface, and the hydrophobic interior of the lipid bilayer can all be used as templates.

Generally, after formation of liposomes of the desired size, a hydrophobic monomer, for example, is dispersed in the hydrophobic interior of the lipid bilayer of the liposomes. The monomer is crosslinked and the liposomal material is removed, leaving the hollow polymeric particle.

Methods of making liposomes, and controlling the size and shape thereof, are well known to those skilled in the art. Liposomal preparations typically have a broad size distribution. A more controlled size variation can be achieved using extrusion, for example.

The mean size of the pores (and simultaneously the extent of the swelling of the particles) can be directly controlled by the crosslinking density, i.e. the mesh-size of the network structure.

Incorporation of Active Agents

Large quantities of substances can be incorporated into the central cavity of the hollow particles. Active agents can be encapsulated into the polymer by different routes. In one method, the agent may be directly added to the copolymer during preparation of the copolymer. For example, the compound may be dissolved together with the polymer in ethanol. In a second method, the drug is incorporated into the copolymer after assembly and optionally covalent crosslinking. The hollow particles can be isolated from the aqueous solution and redissolved in a solvent such as ethanol. Ethanol is a good solvent for the hydrophilic and the hydrophobic parts of some polymers. Hence, the polymer shell of the hollow particles swells in ethanol and becomes permeable. Transferring the particles back into water decreases the permeability of the shell.

The encapsulation of compounds can not only be achieved by changes in the solvent but also by changes in temperature, pH, and ionic strength. The particles are generally loaded in the swollen (permeable) state, then their permeability is decreased by external stimuli. Afterwards, the loaded particles can be isolated.

The present invention will be further understood by reference to the following non-limiting examples.

EXAMPLES

Example 1

Encapsulation of Pyrene-Labeled PEO in Poly (acrylic acid) Hollow Particles

This example is illustrated by a schematic in FIG. 1.

Preparation of Hollow Particles

Small unilamellar vesicles with diameters in the range of 200–300 nm were prepared by ultrasonification (1 h at 60° C.) of an aqueous solution containing $3.7 \times 10^{-2}$ molL$^{-1}$ of the lipid dimethyldiocatdecylammonium chloride (DODAC). A 60 mL portion of the resulting vesicle solution was swollen with 0.300 g tert-butylacrylate, 3.5 mg divinyl benzene, and a small crystal of the free radical initiator azoisobutyronitrile (AIBN). Purified argon was bubbled through the solution to eliminate oxygen. The mixture was tempered 2 hours at 55° C. prior to UV-induced polymerization (Ultratech 400 W, λ of 254 nm; Osram AG, time of irradiation was 5 minutes). The surfactant was removed by precipitating the polymer in methanol. The polymer was redissolved in tetrahydrofuran and reprecipitated in methanol until $^1$H-NMR indicated the absence of surfactant. The resulting polymer was dissolved in 25 mL dioxane and 1 mL of concentrated hydrochloric acid was added. The mixture was heated to 90° C. for 6 hours. The resulting poly(acrylic acid) hollow spheres were isolated by precipitation in diethylether. The yield was 93%.

Incorporation of Pyrene Labeled PEO

The poly(acrylate) hollow particles were incubated with pyrene-labeled polyethylene oxide (PEO) ($M_o$=5000 gmol$^{-1}$), at a concentration of 2 micromolar at pH 9.0. The pH was then lowered to pH 4 by dialysis, which also removed any non-encapsulated pyrene labeled PEO. The pH of the suspension was then increased to pH 9 and the hollow particles dialyzed at pH 9 to remove the released pyrene labeled PEO.

The control was poly(acrylate) microspheres incubated with pyrene labeled PEO at a concentration of 2 micromolar at pH 4 and dialyzed at pH 4 to remove non-encapsulated pyrene labeled PEO.

Fluorescence Spectra

Fluorescence spectra of the "loaded" particles showed that pyrene labeled PEO was definitely encapsulated in the interior of the hollow particles, with no adsorption of the polymer on the particle surface. Spectra of the poly(acrylate) hollow particles at pH 4 (excitation at 345 nm) when "emptied" showed that the encapsulation process was completely reversible.

The radius of the poly(acrylic acid) hollow spheres in water was about 25 nm at pH 4 and about 100 nm at pH9.

This study demonstrates that pH responsive particles were formed at pH 4, that drug was loaded at a high pH (pH 9), that the drug remained encapsulated and the particles were stable when the pH was reduced, and that the particles expanded and released the labeled PEO at pH 9. The study also demonstrated that drug can be released based on pH.

Example 2

Addition of Hydrophobic Comonomers

The swelling isotherms of poly(acrylic acid) hollow spheres as a function of pH were measured. Citrate buffer was used for pH less than 7 and phosphate buffer was used for pH greater than 7. The total ionic strength was 0.1M, set by addition of NaCl. The effect of the addition of t-butyl-methacrylate on the swelling isotherms was determined for 25%, 50%, and 75% t-butyl-methacrylate.

Figure 2:
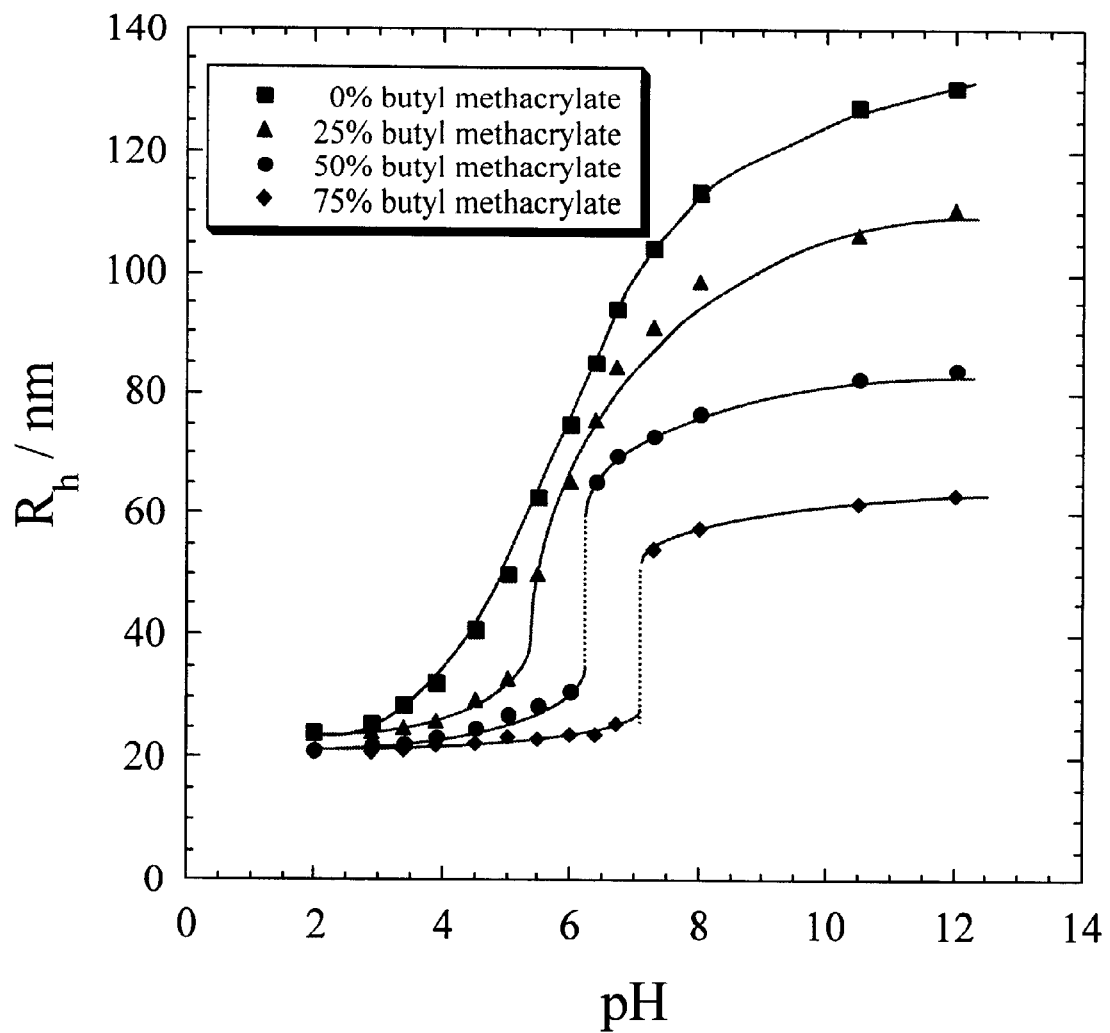
FIG. 2 illustrates swelling isotherms of poly(acrylic acid) hollow particles as a function of pH in citrate (pH less than 7) and phosphate (pH greater than 7) buffers at total ionic strength of 0.1M, set by addition of NaCl, and the effect of the addition of t-butyl methacrylate on the swelling isotherms. ■: 0% t-butyl methacrylate; ▲: 25% t-butyl methacrylate; ●: 50% t-butyl methacrylate; ♦: 75% t-butyl methacrylate.

The results are illustrated in FIG. 2, where the curve shown by the symbol ■ is 0% t-butyl methacrylate; the curve shown by the symbol ▲ is 25% t-butyl methacrylate; the curve shown by the symbol ● is 50% t-butyl methacrylate; and the curve shown by the symbol ♦ is 75% t-butyl methacrylate.

The introduction of n-butyl-methacrylate comonomers to the responsive material shifted the transition to higher pH values and led to a sharper (first order like) transition.

Example 3

Characterization of Poly(acrylic acid) Hollow Particles

Preparation of Hollow Particles

Small unilamellar vesicles were prepared from the synthetic surfactant dimethyldioctadecyl ammonium chloride (DODAC) by ultrasonification of aqueous lipid dispersions (2.1 wt % DODAC). This yielded unilamellar vesicles with an average diameter of 100 nm; however, with a rather high polydispersity. The lipid bilayers of the vesicles were swollen by incubating them in the presence of hydrophobic monomers (25 wt % with respect to the lipid) for 2 hours at 60° C. A crosslinking polymerization of the monomers was initiated by UV-irradiation (2 hours) at room temperature.

Afterwards the resulting polymer particles were isolated from the vesicles by repeated precipitation in a large excess of methanol to water (3:1) until $^1$H-NMR reflected complete removal of the surfactant. Mixtures of t-butyl acrylate (t-BUA) and ethylene glycol dimethacrylate (EGDMA) were used as the hydrophobic monomers and the crosslinking agent. For selective saponification of the t-butyl ester groups, the crosslinked poly(t-butyl acrylate) hollow spheres were dissolved in dioxane and stirred for 8 h at 80° C. in the presence of a catalytic amount of hydrochloric acid. The resulting poly(acrylic acid) particles were precipitated in diethylether and finally dried by lyophilization from dioxane. $^1$H-NMR indicated full conversion of the poly(t-butyl acrylate) under these conditions.

The resulting poly(acrylic acid) particles were soluble in aqueous media. A characteristic cryogenic electron micrograph (cryo-TEM) of a representative sample in an aqueous phosphate buffer at pH 7 showed clearly that the polymer particles were hollow and no solid latex particles or fragments of the shells were detected. The size of the particles was in good agreement with dynamic light scattering experiments and they were polydisperse as were the parent DODAC vesicles. This reflects that the newly formed poly (acrylic acid) hollow spheres survived intactly the isolation and saponification procedure.

The sensitivity of the particles towards changes of the pH and/or ionic strength of the buffer is the basic requirement for their use as controlled release devices. Therefore the behavior of the poly(acrylic acid) hollow spheres in phosphate buffers of varying pH was examined. The pH-induced dimensional changes of the particles were investigated by dynamic light scattering. The ionic strength of the buffers used for these experiments was carefully kept constant at 0.1 M by addition of sodium chloride. Although electrostatic interactions are shielded considerably, this salt concentration is close to physiological conditions (about 150 mM), which is the relevant range for most pharmaceutical applications. Additionally the systems are quite insensitive towards small ionic impurities at this concentration.

Figure 3:
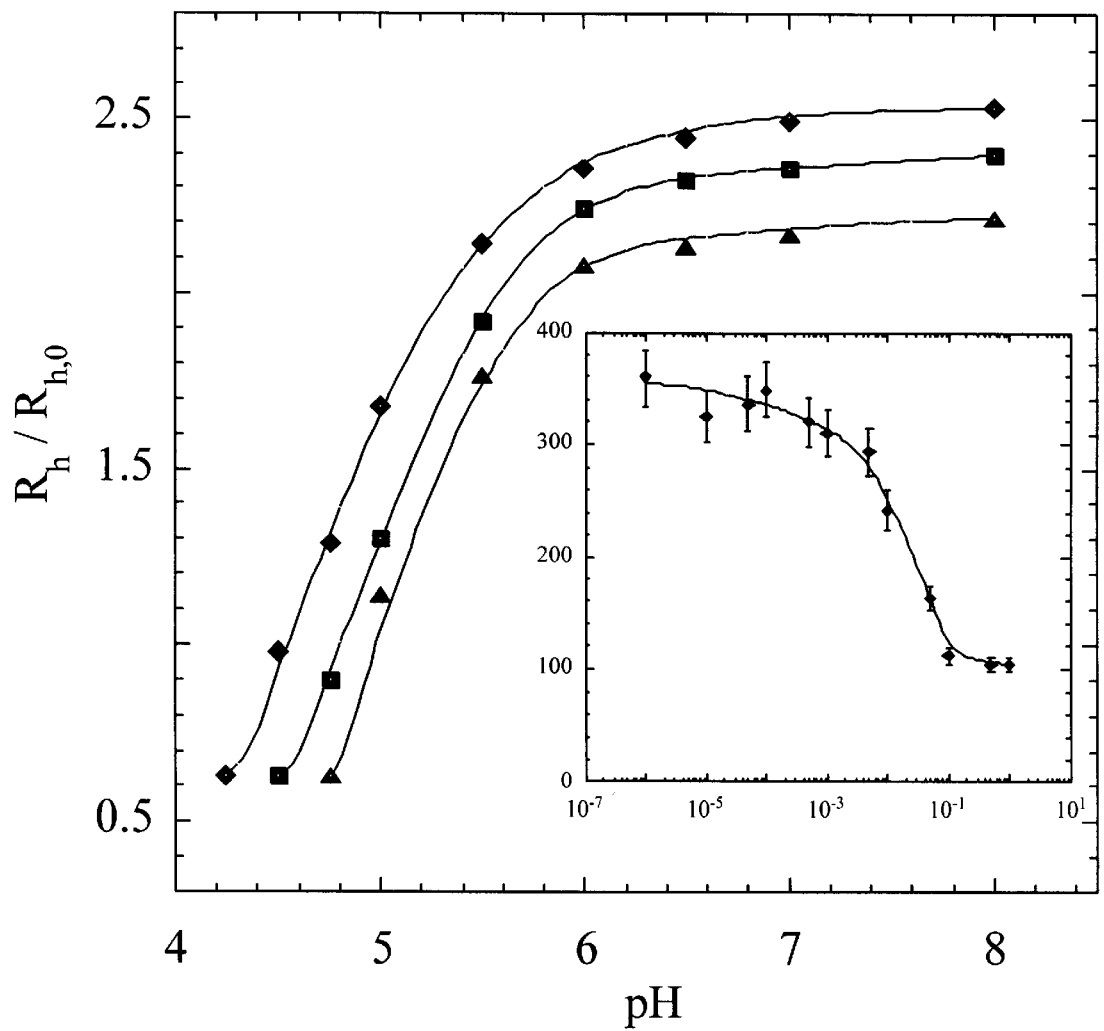
FIG. 3 illustrates the reduced hydrodynamic radius $R_h/R_{h,0}$ ($R_h$: hydrodynamic radius of poly(acrylic acid) hollow spheres; $R_{h,0}$: hydrodynamic radius of the polymer containing vesicular precursors) as a function of pH. The different curves correspond to particles with a different molar fraction of the crosslinking comonomer ethylene glycol dimethacrylate (EGDMA). ▲: 3 mole % EGDMA ($R_{h,0}$=49 nm); ■: 5 mole % EGDMA ($R_{h,0}$=55 nm); ▲:10 mole % EGDMA ($R_{h,0}$=60 nm). The inset illustrates the hydrodynamic radius $R_h$ of poly(acrylic acid) hollow spheres (5 mole % EGDMA) as a function of salt concentration ($c_{salt}$) of the buffer.

To take into account small variations in the average radius of different batches of the precursor vesicles a reduced hydrodynamic radius $R_h/R_{h,0}$ ($R_h$: hydrodynamic radius of poly(acrylic acid) hollow spheres; $R_{h,0}$: hydrodynamic radius of the polymer containing vesicular precursors) was plotted as a function of pH. FIG. 3 illustrates the results. The curve shown by the symbol ♦ is 3 mole % EGDMA ($R_{h,0}$=49 nm); the curve shown by the symbol ■ is 5 mole % EGDMA ($R_{h,0}$=55 nm); the curve shown by the symbol ▲ is 10 mole % EGDMA ($R_{h,0}$=60 nm).

The dimensions of the particles increased considerably with increasing pH. In the range from pH 4 to pH 8 the radius increased up to a factor of about 4 (the encapsulated volume increased by a factor of 64). This swelling was completely reversible.

The different curves in FIG. 3 refer to particles of different crosslinking density, which was controlled by the molar fraction of the crosslinker EGDMA in the particles. With increasing crosslinking density the maximum swelling decreased and the swelling transition shifted towards a higher pH. It is important to note that the poly(acrylic acid) hollow particles precipitate at low pH. The first points of the different curves in FIG. 3 represent the lowest pH, respectively, for which stable particle dispersions were obtained. Such a pH-induced precipitation could be highly interesting for applications since it represents a convenient way to separate the particles after their loading from the solution.

The effect of varying salt (NaCl) concentration is shown in the inset of FIG. 3. Throughout this series of measurements the pH was kept constant at pH 6, where the poly (acrylic acid) is highly ionized. With decreasing salt concentration the swelling of the particles increased and tended towards a saturation value. This is due to decreasing electrostatic shielding effects. An increase of the radius of the poly(acrylic acid) hollow particles up to a factor of 10 (an increase in the encapsulated volume by a factor of 1000) can be predicted at low salt concentrations.

Example 4

Emulsion Polymerization for Making Responsive Hollow Particles

Latex particles were prepared using a two-stage emulsion polymerization technique. A three-necked 250 ml flask equipped with a 50 ml dropping funnel and a mechanic stirring arm was used. The polymerization was performed as a semi-batched process with continuous addition of the second stage monomer mixture. In the first stage the monomer 2-ethylhexyl methacrylate was polymerized with addition of 2 mol % $CBr_4$ as chain transfer agent. The whole reaction was carried out under oxygen free conditions using degassed and deionized water as a solvent. The precise recipe for the reaction is given in the following table.

TABLE 1

Standard recipe for latex preparation

| First step | |
|---|---|
| Sodium Lauryl Sulfate | 0.2 g |
| Water | 80 g |
| Potassium Persulfate | 0.1 g |
| 2-Ethylhexyl Methacrylate | 20 g |
| Tetrabromomethane | 0.66 g |
| Temperature | 70° C. (should not be above 85° C.) |
| Time | 150 min |
| Diameter of the core particle | 100 nm |
| Second step | |
| Tert.-Butyl Acrylate | 20 g |
| Ethylene glycol dimethacrylate | 315 mol % of Tert.-butyl Acrylate |
| Feed Rate | 0.25 mL/min |
| Temperature | 70° C. (should not be above 85° C.) |
| Time | 300 min |
| Diameter of the core-shell particle | 120 nm |

To remove the core material the resulting particles were precipitated in methanol (1000 ml) and redissolved in dioxane (100 ml), heated up to about 85° C., and maintained for three hours with continuous agitation. After addition of a catalytic amount of concentrated hydrochloric acid, the mixture was stirred for additional eight hours at 85° C., and then allowed to cool down to ambient temperature. Precipitation in ethyl acetate (1000 ml) resulted in saponified poly(acrylic acid) hollow spheres. This procedure was repeated until no core material could be detected in the ethyl acetate residue (about three to five times). The yield was 10 g of poly(acrylic acid) hollow particles. Experimental data obtained from dynamic light scattering showed an increase in the particle radius from 70 to about 140 nm within a pH range of from 4.5 to 8.0.

Modifications and variations of the present invention will be apparent to those skilled in the art from the forgoing detailed description. All modifications and variations are intended to be encompassed by the following claims. All publications, patents, and patent applications cited herein are hereby incorporated by reference in their entirety.

What is claimed is:

1. A composition for delivery of an agent comprising a hollow particle that undergoes a change in permeability to the agent in response to a stimulus, wherein the hollow particle is formed of a copolymer comprising a stimulus responsive triblock ABA or BAB copolymer that is amphiphilic, wherein A is a hydrophilic block and B is a hydrophobic block.

2. The composition of claim 1 wherein the stimulus responsive triblock copolymer undergoes a conformation change when exposed to a change in a stimulus selected from the group consisting of pH, temperature, light, ionic strength, electric field, magnetic field, and solvent composition.

3. The composition of claim 1 wherein the agent is selected from the group consisting of therapeutic, prophylactic, and diagnostic agents.

4. The composition of claim 1 wherein the agent is selected from the group consisting of cosmetic agents, fragrances, dyes, pigments, photoactive compounds, and chemical reagents.

5. The composition of claim 1 wherein the agent is selected from the group consisting of metal particles, biological polymers, nanoparticles, biological organelles, and cell organelles.

6. The composition of claim 1, wherein the particle is formed by templating.

7. The composition of claim 1 wherein the particle is formed by self-assembly in a solvent.

8. The composition of claim 1, wherein the particle comprises a ligand for targeting the particle.

9. The composition of claim 1, wherein the change in permeability of the particle is reversible.

10. The composition of claim 1, wherein the change in permeability of the particle is due to a change in the size of the particle.

11. A method for manufacture of a composition for delivery of an agent comprising encapsulating the agent into a hollow particle that undergoes a change in permeability to the agent in response to a stimulus, wherein the hollow particle is formed of a copolymer comprising a stimulus responsive triblock ABA or BAB copolymer that is amphiphilic, wherein A is a hydrophilic block and B is a hydrophobic block.

12. The method of claim 11 wherein the agent is encapsulated by exposing the particle to a stimulus in an amount effective to increase the permeability of the particle in the presence of the agent to be encapsulated, and then decreasing the permeability of the particle.

13. The method of claim 11 wherein the stimulus responsive triblock copolymer undergoes a conformation change when exposed to a change in a stimulus selected from the group consisting of pH, temperature, light, ionic strength, electric field, magnetic field, and solvent composition.

14. The method of claim 11 wherein the agent is selected from the group consisting of therapeutic prophylactic and diagnostic agents.

15. The method of claim 11 wherein the agent is selected from the group consisting of cosmetic agents, fragrances, dyes, pigments, photoactive compounds, and chemical reagents.

16. The method of claim 11 wherein the agent is selected from the group consisting of metal particles, biological polymers biological organelles, and cell organelles.

17. The method of claim 11 wherein the method comprises forming the particle by self-assembly in a solvent, by adding, the agent to the solvent prior to or at the time of encapsulation.

18. The method of claim 11 wherein the particle is formed by templating.

* * * * *